US008517241B2

(12) United States Patent
Nicholas et al.

(10) Patent No.: US 8,517,241 B2
(45) Date of Patent: Aug. 27, 2013

(54) HAND-HELD SURGICAL DEVICES

(75) Inventors: David Nicholas, Trumball, CT (US);
Donald Malinouskas, Monroe, CT
(US); David Zeichner, Oxford, CT (US)

(73) Assignee: Covidien LP, Mansfield, MA (US)

( * ) Notice: Subject to any disclaimer, the term of this patent is extended or adjusted under 35 U.S.C. 154(b) by 293 days.

(21) Appl. No.: 13/039,677

(22) Filed: Mar. 3, 2011

(65) Prior Publication Data
US 2011/0253765 A1 Oct. 20, 2011

Related U.S. Application Data

(60) Provisional application No. 61/324,919, filed on Apr. 16, 2010.

(51) Int. Cl.
*A61B 17/068* (2006.01)
(52) U.S. Cl.
USPC ..... 227/175.3; 227/19; 227/179.1; 227/175.1
(58) Field of Classification Search
USPC ............................ 227/175.1, 19, 179.1, 175.3
See application file for complete search history.

(56) References Cited

U.S. PATENT DOCUMENTS

| 5,339,799 | A | 8/1994 | Kami et al. | |
|---|---|---|---|---|
| 6,264,087 | B1 * | 7/2001 | Whitman | 227/180.1 |
| 6,315,184 | B1 * | 11/2001 | Whitman | 227/180.1 |
| 6,443,973 | B1 * | 9/2002 | Whitman | 606/219 |
| 6,698,643 | B2 | 3/2004 | Whitman | |
| 6,716,233 | B1 | 4/2004 | Whitman | |
| 6,793,652 | B1 | 9/2004 | Whitman et al. | |
| 6,846,307 | B2 | 1/2005 | Whitman et al. | |
| 6,846,308 | B2 | 1/2005 | Whitman et al. | |
| 6,846,309 | B2 | 1/2005 | Whitman et al. | |
| 6,849,071 | B2 | 2/2005 | Whitman et al. | |
| 6,981,941 | B2 | 1/2006 | Whitman et al. | |
| 7,077,856 | B2 | 7/2006 | Whitman | |
| 7,481,347 | B2 * | 1/2009 | Roy | 227/175.1 |
| 7,721,936 | B2 | 5/2010 | Shalton, IV et al. | |

(Continued)

FOREIGN PATENT DOCUMENTS

| EP | 1943954 A2 | 7/2008 |
|---|---|---|
| EP | 1943956 A2 | 7/2008 |

(Continued)

OTHER PUBLICATIONS

European Search Report for corresponding EP11250473 date of mailing is Aug. 3, 2011 (3 pages).

*Primary Examiner* — Brian D Nash

(57) ABSTRACT

A surgical system is provided and includes an intelligent surgical device having a drive motor supported in the housing and being in electrical communication with the power source; and control circuitry. The control circuitry includes a feedback system for monitoring a condition of the surgical device during a use thereof and for changing an operative parameter of the surgical device when a change in the monitored condition occurs. The surgical system includes a non-intelligent loading unit for selective connection to the housing of the surgical device and which is actuatable by the drive motor, the loading unit having a first and a second condition. During operation, the drive motor actuates the loading unit from the first condition to the second condition; and when the loading unit achieves the second condition, a change in the at least one monitored condition occurs and an operative parameter of the surgical device is changed.

11 Claims, 6 Drawing Sheets

(56) References Cited

U.S. PATENT DOCUMENTS

| | | | |
|---|---|---|---|
| 2002/0165541 A1* | 11/2002 | Whitman | 606/48 |
| 2003/0125717 A1 | 7/2003 | Whitman | |
| 2004/0111081 A1 | 6/2004 | Whitman et al. | |
| 2005/0192609 A1 | 9/2005 | Whitman et al. | |
| 2006/0151567 A1* | 7/2006 | Roy | 227/175.1 |
| 2007/0055304 A1 | 3/2007 | Whitman | |
| 2007/0102473 A1* | 5/2007 | Shelton et al. | 227/175.1 |
| 2007/0175956 A1* | 8/2007 | Swayze et al. | 227/178.1 |
| 2007/0175961 A1* | 8/2007 | Shelton et al. | 227/178.1 |
| 2007/0175964 A1* | 8/2007 | Shelton et al. | 227/180.1 |
| 2007/0187453 A1* | 8/2007 | Smith et al. | 227/175.1 |
| 2008/0078801 A1* | 4/2008 | Shelton et al. | 227/175.1 |
| 2008/0277449 A1* | 11/2008 | Marczyk | 227/176.1 |
| 2008/0308607 A1* | 12/2008 | Timm et al. | 227/176.1 |
| 2009/0090763 A1* | 4/2009 | Zemlok et al. | 227/175.2 |
| 2009/0099876 A1 | 4/2009 | Whitman | |
| 2009/0101692 A1 | 4/2009 | Whitman et al. | |
| 2011/0121049 A1 | 5/2011 | Malinouskas et al. | |
| 2011/0125138 A1 | 5/2011 | Malinouskas et al. | |

FOREIGN PATENT DOCUMENTS

| | | |
|---|---|---|
| EP | 2044890 A1 | 4/2009 |
| EP | 2272443 A1 | 1/2011 |
| WO | WO 2009/039506 A1 | 3/2009 |
| WO | WO 2009/143092 A1 | 11/2009 |

* cited by examiner

HAND-HELD SURGICAL DEVICES

CROSS REFERENCE TO RELATED APPLICATION

The present application claims the benefit of and priority to U.S. Provisional Application Ser. No. 61/324,919 filed on Apr. 16, 2010, the entire contents of which are incorporated herein by reference.

BACKGROUND

1. Technical Field

The present disclosure relates to surgical devices and/or systems. More specifically, the present disclosure relates to hand-held surgical devices and/or systems configured for use with removable disposable loading units and/or single use loading units for clamping, cutting and/or stapling tissue.

2. Background of Related Art

A number of surgical device manufacturers have developed product lines with proprietary drive systems for operating and/or manipulating the surgical device. In many instances the surgical devices include a handle assembly, which is reusable, and disposable loading units and/or single use loading units or the like that are selectively connected to the handle assembly prior to use and then disconnected from the handle assembly following use in order to be disposed of or in some instances sterilized for re-use.

In intelligent surgical devices, intelligent disposable loading units and/or single use loading units include an identification element which communicates with a reader element disposed within an intelligent powered handle assembly. In this manner, when the intelligent disposable loading units and/or single use loading units are connected to the intelligent handle assembly, the reader element of the intelligent handle assembly communicates with the identification element of the intelligent disposable loading units and/or single use loading units to thereby indicate to the intelligent handle assembly which particular loading unit is attached thereto. Once the particular loading unit, attached to the handle assembly is identified, operative parameters for the powered handle assembly may be set in accordance with predetermined values.

A need exists for a system that is able to detect particular parameters (e.g., length of a staple cartridge, indication that a staple cartridge has been fired) of non-intelligent (i.e., not including an identification member) disposable loading units and/or single use loading units when such non-intelligent disposable loading units and/or single use loading units are connected to intelligent handle assemblies.

SUMMARY

The present disclosure relates to hand-held surgical devices and/or systems configured for use with removable disposable loading units and/or single use loading units for clamping, cutting and/or stapling tissue.

According to an aspect of the present disclosure, a surgical system for performing a surgical procedure is provided. The surgical system includes an intelligent surgical device having a housing; a power source supported in the housing; at least one drive motor supported in the housing and being in electrical communication with the power source; and control circuitry interfacing with the power source and the at least one drive motor. The control circuitry includes a feedback system for monitoring at least one condition of the surgical device during a use thereof and for changing an operative parameter of the surgical device when a change in the at least one monitored condition occurs. The surgical system includes at least one non-intelligent loading unit configured for selective connection to the housing of the surgical device and which is actuatable by the at least one drive motor, the loading unit having at least a first condition and a second condition. During operation of the surgical device, the at least one drive motor actuates the loading unit from the first condition to at least the second condition; and when the loading unit achieves the second condition, a change in the at least one monitored condition occurs and an operative parameter of the surgical device is changed.

The at least one condition monitored by the feedback system may be a voltage being delivered to the at least one drive motor. The feedback system may include a resistor of a known quantity associated with the voltage being delivered to the at least one drive motor. The feedback system may calculate a current level across the resistor.

The operative parameter of the surgical device may be changed when the feedback system determines a current level across the resistor exceeds a threshold current level.

The second condition of the loading unit may be an end of a firing stroke thereof The current level across the resistor may exceed the threshold current level when the end of the firing stroke of the loading unit is reached.

The operative parameter of the surgical device that is changed when the feedback system determines that the current level across the resistor exceeds the threshold current level may be a voltage that is delivered to the at least one drive motor.

The operative parameter of the surgical device that is changed may be a power delivered to the at least one motor.

The second condition of the loading unit may be an end of a firing stroke thereof.

The surgical system may further include a plurality of non-intelligent loading units, wherein each loading unit includes a different unique second condition. The second condition of each loading unit may correspond to a different unique length of a firing stroke of each loading unit. The at least one condition monitored by the feedback system may be a voltage being delivered to the at least one drive motor, wherein the feedback system may include a resistor of a known quantity associated with the voltage being delivered to the at least one drive motor, and wherein the feedback system may calculate a current level across the resistor, and wherein the operative parameter of the surgical device may be changed when the feedback system determines a current level across the resistor exceeds a threshold current level.

The current level across the resistor may exceed the threshold current level when the end of the firing stroke of any of the plurality of loading units is reached. The operative parameter of the surgical device that is changed when the feedback system determines that the current level across the resistor exceeds the threshold current level may be a voltage that is delivered to the at least one drive motor.

BRIEF DESCRIPTION OF THE DRAWINGS

Embodiments of the present disclosure are described herein with reference to the accompanying drawings, wherein.

DETAILED DESCRIPTION OF EMBODIMENTS

Figure 1:
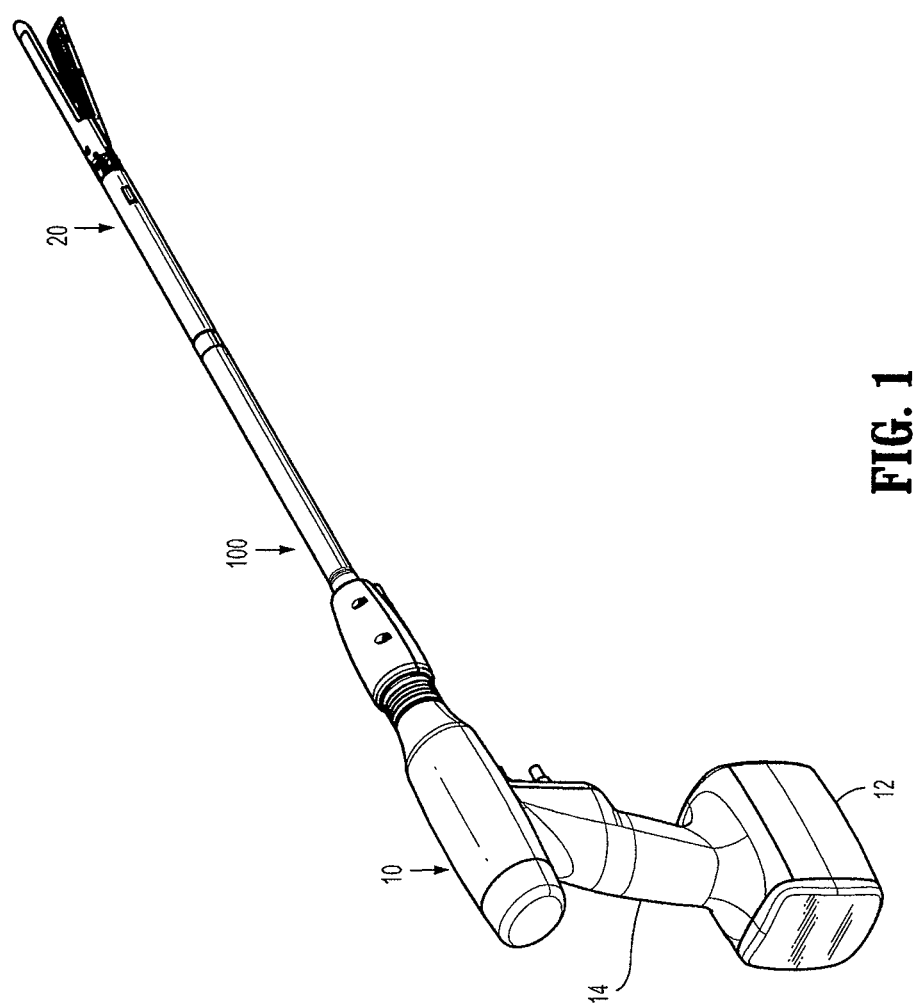
FIG. 1 is a rear, perspective view of an exemplary intelligent surgical device and/or handle assembly supporting an adapter assembly and illustrating an exemplary loading unit supported on an end of the adapter assembly.
Figure 2:
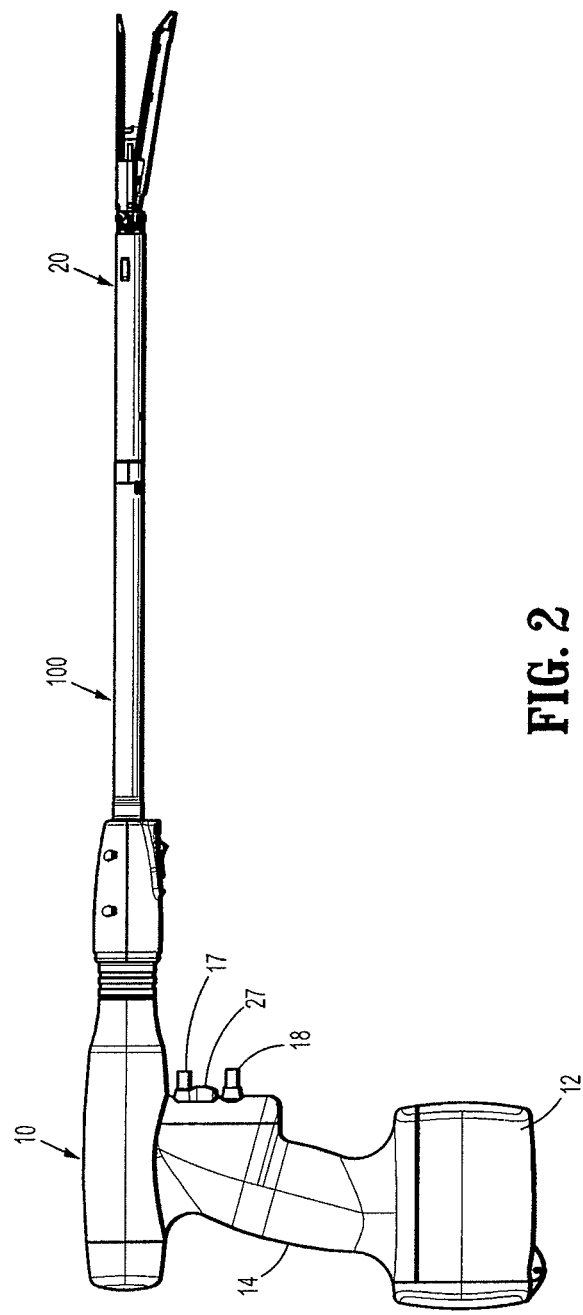
FIG. 2 is a side, elevational view of the intelligent surgical device, adapter assembly and loading unit shown in FIG. 1.
Figure 3:
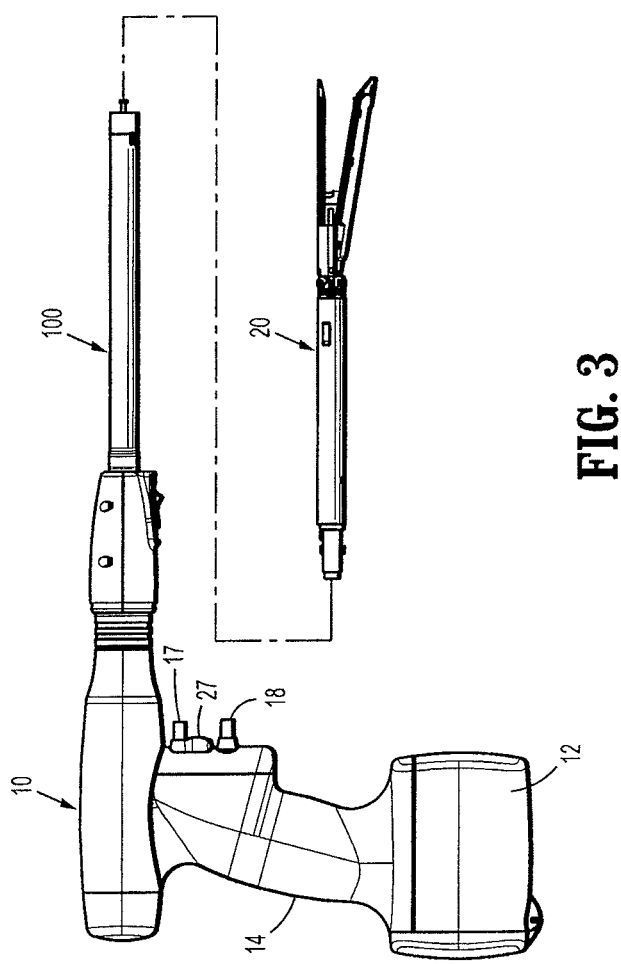
FIG. 3 is a perspective view of the intelligent surgical device of FIGS. 1 and 2, illustrating the adapter assembly connected thereto and illustrating the loading unit disconnected from the adapter assembly.
Figure 4:
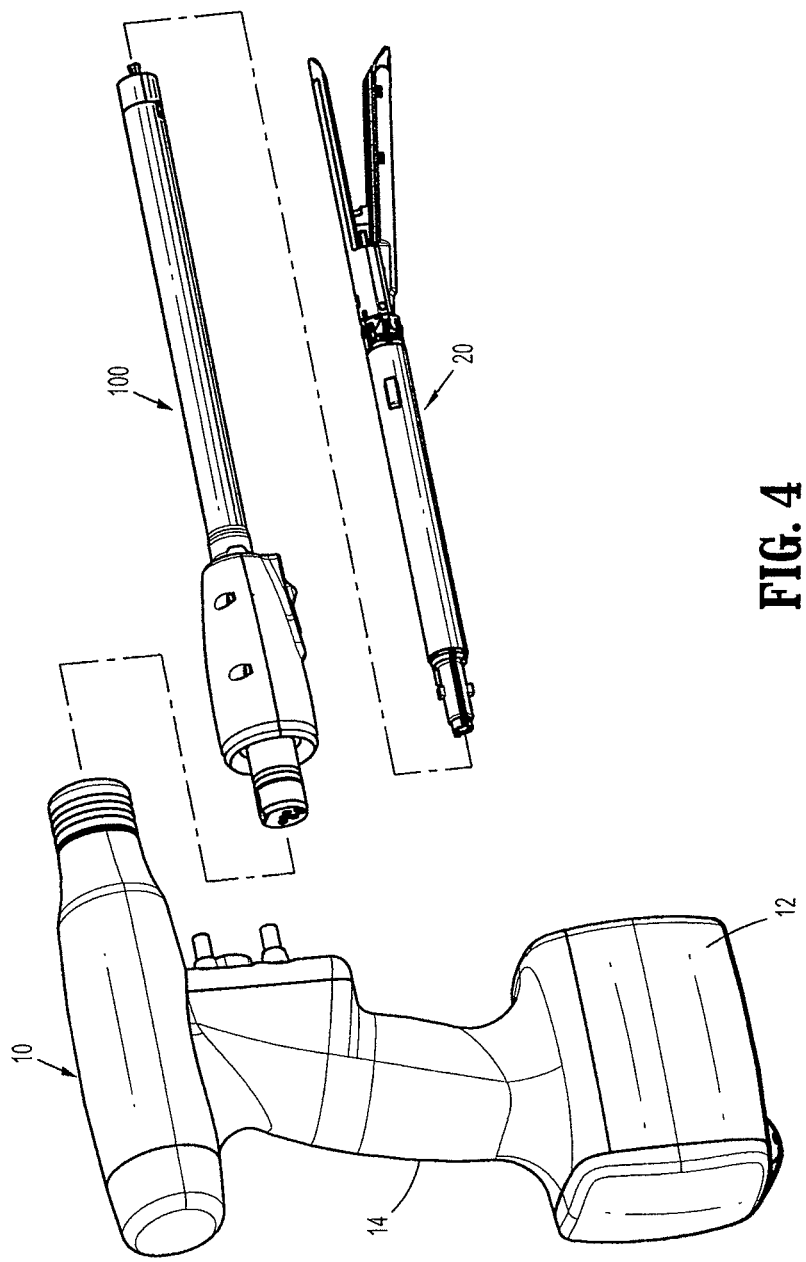
FIG. 4 is a perspective view of the intelligent surgical device of FIGS. 1-3, illustrating the adapter assembly disconnected therefrom and illustrating the loading unit disconnected from the adapter assembly.

Embodiments of the presently disclosed surgical device are described in detail with reference to the drawings, in which like reference numerals designate identical or corresponding elements in each of the several views. As used herein the term "distal" refers to that portion of the surgical device, or component thereof, farther from the user, while the term "proximal" refers to that portion of the surgical device, or component thereof, closer to the user.

Referring initially to FIGS. 1-4, a hand-held powered surgical device in accordance with an embodiment of the present disclosure is shown and generally designated 10. Reference may be made to International Application No. PCT/US2008/077249, filed Sep. 22, 2008 (Inter. Pub. No. WO 2009/039506) and U.S. patent application Ser. No. 12/622,827, filed on Nov. 20, 2009, the entire content of each of which is incorporated herein by reference, for a detailed description of the construction and operation of exemplary surgical devices 10.

Surgical device 10 includes a housing having lower portion 12 forming a base, and an intermediate portion 14, which includes several finger-actuated control buttons 17 and 18 and rocker device 27. Lower portion 12 is configured to selectively store a power source in the form of a battery or the like (not shown). Intermediate portion 14 is configured and adapted to house at least one drive motor (not shown) that is powered by the power source. Surgical device 10 further includes control circuitry (not shown) therein which controls the operation of surgical device 10 based on input from a user and/or feedback obtained prior to, during or after operation of surgical device 10.

Control buttons 17 and 18 and rocker device 27 are located at a front location of the intermediate portion 14 of surgical device 10. Each one of the control buttons 17, 18, and rocker device 27 includes a respective magnet that is moved by the actuation of a user, or operator. In addition, a circuit board (not shown) disposed within surgical device 10 includes, for each one of the control buttons 17, 18 and rocker device 27, respective Hall-effect switches that are actuated by the movement of the magnets in the control buttons 17, 18 and rocker device 27. The actuation of the Hall-effect switch causes the circuit board to provide appropriate signals to a function selection module and an actuator or input drive component to actuate or operate loading unit 20.

Surgical devices 10 may include at least one drive motor, at least one power source "PS" (see FIG. 5) for powering the at least one drive motor, and at least one rotatable drive shaft connected to the drive motor.

In accordance with the present disclosure, surgical device 10 includes a first and a second drive motor, and a first and a second rotatable drive member or shaft, respectively connected to the first and second drive motors. In use, as the first drive motor is activated, the first drive motor will cause the first drive shaft to selectively rotate along its axis in either a first or clock-wise direction, or in a second or counter clock-wise direction. Additionally, as the second drive motor is activated, the second drive motor will cause the second drive shaft to selectively rotate along its axis in either a first or clock-wise direction, or in a second or counter clock-wise direction.

Surgical device 10 is shown in FIGS. 1-4 interfacing with an adapter assembly 100 configured to interconnect surgical device 10 with disposable loading units (DLUs) and/or single use loading units (SULUs) (hereinafter, "loading units"). Reference may be made to U.S. Provisional Application Ser. No. 61/308,045, filed on Feb. 25, 2010, the entire content of which is incorporated herein by reference, for a detailed description of the construction and operation of exemplary adapter assemblies 100.

As seen in FIGS. 1-4, adapter assembly 100 is configured and adapted to operatively interconnect and couple any one of a number of loading units to surgical device 10. For example, adapter assembly 100 is configured and adapted to operatively interconnect and couple an endo-gastrointestinal anastomosis loading unit 20 including a staple line length of 30 mm, 45 mm or 60 mm.

Reference may be made to U.S Patent Publication No. 2009/0145947, filed Jan. 14, 2009, the entire content of which is incorporated herein by reference for a detailed discussion of the construction and operation of the endo-gastrointestinal anastomosis loading unit 20.

Loading units 20 include at least one axially translatable drive member therein that is configured and adapted to at least one of open and close jaw assemblies thereof by approximating or separating an anvil assembly and a cartridge assembly to/away from one another, and to fire the loading unit to expel staples contained in the cartridge assembly for formation against the anvil assembly and possibly to actuate a knife blade along the staple line. Loading units 20 may further include an axially translatable drive member therein that is configured and adapted to cause an articulation thereof.

Loading units 20 are non-intelligent in that loading units 20 typically do not include any identification members, in the form of sensors or the like, which interact with reader elements disposed in surgical device 10 for identification thereof and for identification of parameters (e.g., length of a staple cartridge, indication that a staple cartridge has been fired) thereof.

Figure 5:
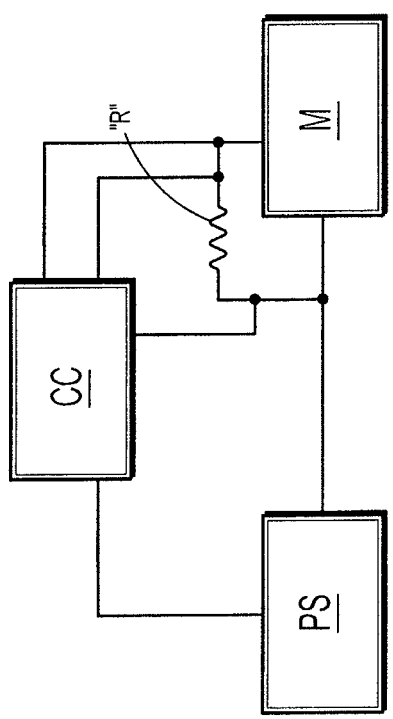
FIG. 5 is a schematic of a circuit diagram of a feedback system according to an embodiment of the present disclosure.

In accordance with the present disclosure, in order for intelligent surgical device 10 to identify the parameters of non-intelligent loading units 20, intelligent surgical device 10 includes, as seen in FIG. 5, a feedback system incorporated into or associated with the drive circuit or control circuit "CC" of the first drive motor "M" or second drive motor "M" of intelligent surgical device 10.

It is contemplated, in accordance with an embodiment of the present disclosure, the feedback system incorporates a highly toleranced resistor "R" with an extremely low resistance, about 0.05 ohms, that is added to a low side of an H-bridge responsible for driving the first drive motor or the second drive motor. In operation, the feedback system measures a voltage "V" across resistor "R." By measuring the voltage "V" drop across resistor "R," the feedback system may calculate an amount of current "I" flowing through resistor "R" using Ohm's Law:

$$V=IR$$

In a DC electric motor, such as first drive motor or second drive motor, current "I" is directly related to the amount of torque "τ" being developed by using a relation, e.g., the Torque Constant (Km). Accordingly, the feedback system calculates the amount of torque "τ" being applied to first drive motor or second drive motor according to the following equation:

$$\tau=(Km)(I)$$

By factoring in the reductions in a transmission of surgical device 10 and of a screw drive of surgical device 10, the feedback system may determine an amount of linear force being applied to a firing rod in loading unit 20. Additionally, the feedback system needs to determine a linear position of the firing rod of loading unit 20 in order to ultimately determine if the torque being applied to first drive motor or second drive motor corresponds to a particular length of a staple cartridge loaded in loading unit 20. It is contemplated that an optical or magnetic encoder, a linear variable differential transformer (LVDT) or other method may be used to determine the linear position of the firing rod.

Figure 6:
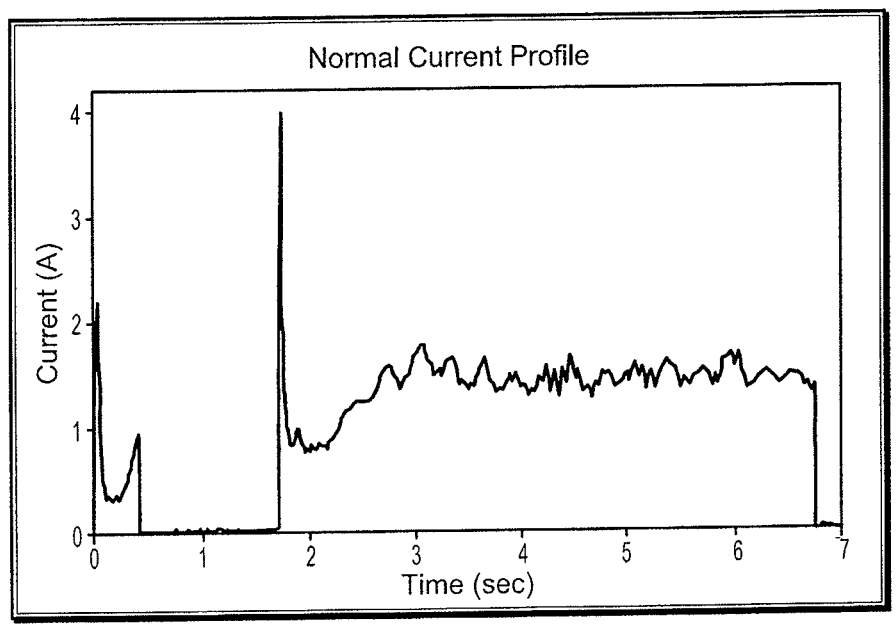
FIG. 6 is a chart illustrating a normal operating profile of current v. time for an intelligent surgical device operating an intelligent loading unit.

During a normal operating condition of surgical device 10, a certain or predetermined force profile is expected to be seen by the feedback system in the control circuitry of surgical device 10, e.g., either a current v. time profile (see FIG. 6) or a current v. distance profile (not shown). In operation, with the control circuitry monitoring current "I," when the firing rod of surgical device 10 is at a linear position corresponding with an end of a stroke for a particular staple cartridge length (i.e., 30 mm, 45 mm or 60 mm) and the feedback system of the control circuitry determines a higher than expected current "I" or current spike (as seen in FIG. 7), the control circuitry can reasonably assume that a firing sled of loading unit 20 has reached an end or a stop of the staple cartridge and/or loading unit 20.

Figure 7:
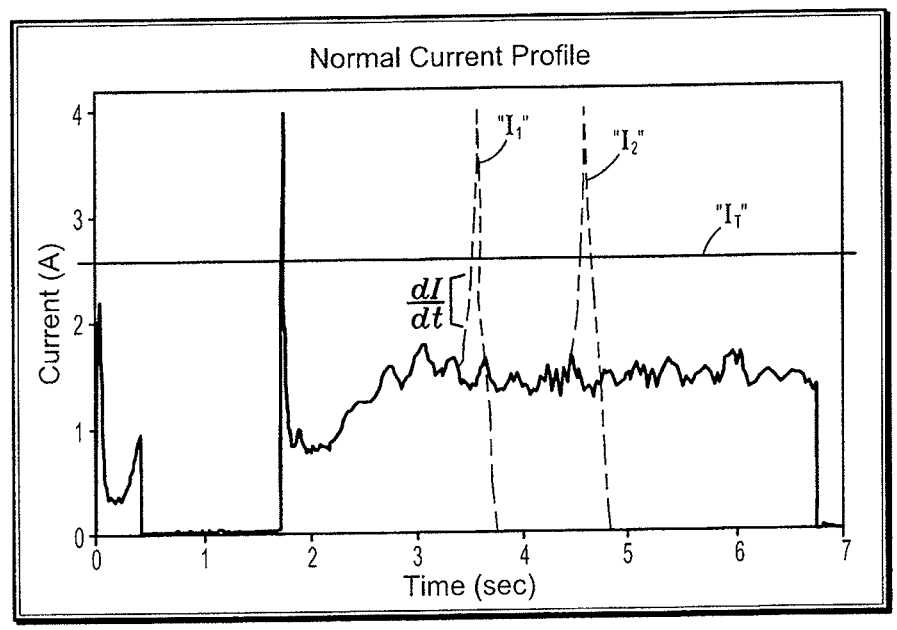
FIG. 7 is a chart illustrating an operating profile of current v. time for an intelligent surgical device operating a non-intelligent loading unit.

As seen in FIG. 7, a first current spike "$I_1$" is illustrated at a location when the firing sled of loading unit 20 has reached an end or a stop of the staple cartridge and/or loading unit 20 corresponding to approximately 30 mm. As also seen in FIG. 7, a second current spike "$I_2$" is illustrated at a location when the firing sled of loading unit 20 has reached an end or a stop of the staple cartridge and/or loading unit 20 corresponding to approximately 45 mm.

Each current spike "$I_1$" or "$I_2$" exceeds a predetermined threshold level "$I_T$" for current "I." The predetermined threshold level "$I_T$" for current "I" is selected so that if there is an increase in current "I" during the firing sequence, at a location prior to 30 mm for a 30 mm staple cartridge, prior to 45 mm for a 45 mm staple cartridge, or prior to 60 mm for a 60 mm staple cartridge, that surgical device 10 will continue to fire until the end or stop of the staple cartridge and/or loading unit 20 has been achieved, as described above. Premature increases in current "I," during the firing of surgical device 10, may be experienced if the path through the tissue through which loading unit 20 is acting on includes a segment of denser tissue, a change in the type of tissue, a prior deployed fastener or the like.

Additionally or alternatively, the control circuitry of surgical device 10 may also monitor a slope of current v. time (dI/dt) or current v. distance (dI/dx) to determine if an end of the staple cartridge has been reached. For example, if the feedback system determines that a rise in the slope has become excessively large, the control circuitry can also reasonably assume that a firing sled of loading unit 20 has reached an end or a stop of the staple cartridge and/or loading unit 20.

In accordance with the present disclosure, the control circuitry of surgical device 10 includes a loading unit lockout recognition system that functions and/or operates according to the same or similar principles to the feedback system described above. The loading unit lockout recognition system functions to determine whether a mechanical lockout of a staple cartridge loaded into loading unit 20 has been or has not been activated.

In use, the first time that a staple cartridge is loaded into loading unit 20 and the loading unit 20 is clamped by surgical device 10, surgical device 10 continues to drive forward slightly further than a clamped position for loading unit 20. If the loading unit lockout recognition system measures a sudden spike in current "I," corresponding to a rapid increase in torque "τ," the loading unit lockout recognition system of the control circuitry determines that a hard stop for the mechanical lockout of the staple cartridge in the loading unit 20 has been reached. Surgical device 10 may then relay the information to the user and the control circuitry will not allow surgical device 10 to be fired.

If the loading unit lockout recognition system does not measure a sudden spike in current "I," the loading unit lockout recognition system of the control circuitry concludes that the mechanical lockout of the staple cartridge in the loading unit 20 has not been activated. If the loading unit lockout recognition system concludes that the mechanical lockout of the staple cartridge in the loading unit 20 has not been activated, the control circuitry indicated to the surgical device 10 the presence of an un-fired staple cartridge and operation of surgical device 10 may continue as normal to fire loading unit 20.

It will be understood that various modifications may be made to the embodiments of the presently disclosed adapter assemblies. Therefore, the above description should not be construed as limiting, but merely as exemplifications of embodiments. Those skilled in the art will envision other modifications within the scope and spirit of the present disclosure.

What is claimed is:

1. A surgical system for performing a surgical procedure, the surgical system comprising:
   an intelligent surgical device includes:
      a housing;
      a power source supported in the housing;
      at least one drive motor supported in the housing and being in electrical communication with the power source; and
      control circuitry interfacing with the power source and the at least one drive motor, wherein the control circuitry includes a feedback system for monitoring at least one condition of the surgical device during a use thereof and for changing an operative parameter of the surgical device when a change in the at least one monitored condition occurs, wherein the feedback system includes a resistor of a known quantity associated with a voltage being delivered to the at least one drive motor, and wherein the feedback system calculates a current level across the resistor; and
   at least one non-intelligent loading unit configured for selective connection to the housing of the surgical device and which is actuatable by the at least one drive motor, the loading unit having at least a first condition and a second condition, wherein, during operation of the surgical device, the at least one drive motor actuates the loading unit from the first condition to at least the second condition;

wherein, when the loading unit achieves the second condition, a change in the at least one monitored condition occurs and an operative parameter of the surgical device is changed; and wherein the at least one condition monitored by the feedback system is a voltage being delivered to the at least one drive motor.

2. The surgical system according to claim 1, wherein the operative parameter of the surgical device is changed when the feedback system determines a current level across the resistor exceeds a threshold current level.

3. The surgical system according to claim 2, wherein the second condition of the loading unit is an end of a firing stroke thereof.

4. The surgical system according to claim 3, wherein the current level across the resistor exceeds the threshold current level when the end of the firing stroke of the loading unit is reached.

5. The surgical system according to claim 4, wherein the operative parameter of the surgical device that is changed when the feedback system determines that the current level across the resistor exceeds the threshold current level is a voltage that is delivered to the at least one drive motor.

6. The surgical system according to claim 1, wherein the operative parameter of the surgical device that is changed is a power delivered to the at least one motor.

7. The surgical system according to claim 1, wherein the second condition of the loading unit is an end of a firing stroke thereof.

8. A surgical system for performing a surgical procedure, the surgical system comprising:
  an intelligent surgical device includes:
    a housing;
    a power source supported in the housing;
    at least one drive motor supported in the housing and being in electrical communication with the power source; and
    control circuitry interfacing with the power source and the at least one drive motor, wherein the control circuitry includes a feedback system for monitoring at least one condition of the surgical device during a use thereof and for changing an operative parameter of the surgical device when a change in the at least one monitored condition occurs;
  at least one non-intelligent loading unit configured for selective connection to the housing of the surgical device and which is actuatable by the at least one drive motor, the loading unit having at least a first condition and a second condition, and
  a plurality of non-intelligent loading units, wherein each loading unit includes a different unique second condition;
  wherein, during operation of the surgical device, the at least one drive motor actuates the loading unit from the first condition to at least the second condition;
  wherein, when the loading unit achieves the second condition, a change in the at least one monitored condition occurs and an operative parameter of the surgical device is changed; and
  wherein the second condition of each loading unit corresponds to a different unique length of a firing stroke of each loading unit.

9. The surgical system according to claim 8, wherein the at least one condition monitored by the feedback system is a voltage being delivered to the at least one drive motor, wherein the feedback system includes a resistor of a known quantity associated with the voltage being delivered to the at least one drive motor, and wherein the feedback system calculates a current level across the resistor, and wherein the operative parameter of the surgical device is changed when the feedback system determines a current level across the resistor exceeds a threshold current level.

10. The surgical system according to claim 9, wherein the current level across the resistor exceeds the threshold current level when the end of the firing stroke of any of the plurality of loading units is reached.

11. The surgical system according to claim 10, wherein the operative parameter of the surgical device that is changed when the feedback system determines that the current level across the resistor exceeds the threshold current level is a voltage that is delivered to the at least one drive motor.

* * * * *